(12) United States Patent
Tujii et al.

(10) Patent No.: US 7,401,499 B2
(45) Date of Patent: Jul. 22, 2008

(54) APPARATUS FOR PERMEABILITY ANALYSIS

(75) Inventors: Hirotsugu Tujii, Kyoto (JP); Naohiro Tuboi, Kyoto (JP)

(73) Assignee: GTR Tec Corporation, Kyoto (JP)

( * ) Notice: Subject to any disclaimer, the term of this patent is extended or adjusted under 35 U.S.C. 154(b) by 233 days.

(21) Appl. No.: 11/501,026

(22) Filed: Aug. 9, 2006

(65) Prior Publication Data

US 2007/0101803 A1    May 10, 2007

(30) Foreign Application Priority Data

Aug. 12, 2005   (JP)   ............... 2005-233942
Feb. 7, 2006    (JP)   ............... 2006-029208

(51) Int. Cl.
   *G01N 15/08*   (2006.01)
   *G01M 3/04*    (2006.01)
(52) U.S. Cl. ........................... 73/38; 73/40.7
(58) Field of Classification Search ............ 73/38, 73/40.7, 46, 49.5, 40.5 R
   See application file for complete search history.

(56) References Cited

U.S. PATENT DOCUMENTS

| | | | | |
|---|---|---|---|---|
| 2,255,921 | A | * | 9/1941 | Fear ................................ 73/46 |
| 2,766,614 | A | * | 10/1956 | Cook ............................... 73/46 |
| 4,282,743 | A | * | 8/1981 | Pickett ........................... 73/46 |
| 4,507,954 | A | * | 4/1985 | Boutwell ...................... 73/40.7 |
| 4,879,896 | A | * | 11/1989 | Miller et al. ................... 73/46 |
| 4,893,497 | A | * | 1/1990 | Danielson ..................... 73/40.7 |
| 4,998,435 | A | * | 3/1991 | Miller et al. ................. 73/40.7 |
| 5,209,105 | A | * | 5/1993 | Hasha et al. .................. 73/49.1 |
| 5,309,752 | A | * | 5/1994 | Beckinghausen, Jr. et al. ........................... 73/40.7 |
| 5,375,457 | A | * | 12/1994 | Trapp ........................ 73/40.7 |
| 5,442,952 | A | * | 8/1995 | Morris et al. ................ 73/40.7 |
| 5,447,055 | A | * | 9/1995 | Thompson et al. ........... 73/49.2 |
| 5,728,929 | A |   | 3/1998 | Gevaud |
| 6,073,481 | A | * | 6/2000 | Barefoot ..................... 73/49.5 |
| 6,729,177 | B2 |  | 5/2004 | Shioya et al. |

(Continued)

FOREIGN PATENT DOCUMENTS

EP            0 730 898 A2    9/1996

(Continued)

OTHER PUBLICATIONS

IDS Statement of relevancy, Nov. 16, 2006.

*Primary Examiner*—Hezron E. Williams
*Assistant Examiner*—John Fitzgerald
(74) *Attorney, Agent, or Firm*—Westerman, Hattori, Daniels & Adrian, LLP.

(57) ABSTRACT

An apparatus for permeability analysis which transmits a testing fluid to the tubular specimen and measures the volume of the testing fluid permeating through the tubular specimen. The apparatus for permeability analysis has a tubular specimen, a cylindrical frame, a carrier gas flow inlet leading from the outside of the cylindrical frame to the inside of the cylindrical frame, a carrier gas flow outlet leading from the inside of the cylindrical frame to the outside of the cylindrical frame, a detection device, and a pump. One end of the tubular specimen and the other end of the tubular specimen are connected to each other via the pump. The apparatus for permeability analysis circulates a testing fluid through the tubular specimen continuously or intermittently by means of a pump, conveys the permeate to the detection device by means of the flow of the carrier gas, and then measures the permeate.

4 Claims, 3 Drawing Sheets

U.S. PATENT DOCUMENTS

2003/0037596 A1 * 2/2003 Sorensen .................. 73/40.7

FOREIGN PATENT DOCUMENTS

| JP | 05-223724 A | 8/1993 |
|---|---|---|
| JP | 09-155160 A | 6/1997 |
| JP | 10-260104 A | 9/1998 |
| JP | 2001-059794 A | 3/2001 |
| JP | 2001-232740 A | 8/2001 |
| JP | 2002-005777 A | 1/2002 |
| JP | 2002-224544 A | 8/2002 |
| JP | 2003-121296 A | 4/2003 |
| JP | 2004-157007 A | 6/2004 |
| JP | 2005-055263 A | 3/2005 |
| JP | 2005-156299 A | 6/2005 |
| WO | WO 99/24806 | 5/1999 |

* cited by examiner

APPARATUS FOR PERMEABILITY ANALYSIS

BACKGROUND OF THE INVENTION

1. Field of the Invention

The present invention relates to an apparatus for permeability analysis transmitting a testing fluid into a tubular specimen and measuring quantity and/or quality of the testing fluid permeating through the tubular specimen.

2. Description of the Prior Art

Fuels, lubricants, pressure transmission fluids and the like permeating through tubes, etc. of vehicles contain air-polluting VOCs (volatile organic compounds) and are subject to regulations. VOC is a generic term used to refer to a chemical that evaporates at 50° C. to 260° C. VOCs include aliphatic hydrocarbons, aromatic hydrocarbons, aldehydes, and ketones. However, in the present invention and this specification, VOCs include chemicals defined above and also those that evaporate at a higher or lower temperature than the temperature range described above.

SHED (Sealed Housing for Evaporative Determination) and Mini-SHED are well known as devices for measuring VOCs. SHED is a device for measuring VOCs collected in a closed metal or glass chamber where a vehicle to be tested is encapsulated. Mini-SHED is a device for measuring VOCs collected in a closed metal or glass chamber where a tube, a fuel tank, etc. to be tested is encapsulated.

SUMMARY OF THE INVENTION

In conventional SHEDs or Mini-SHEDs, a chamber used for determining permeability characteristics of a tube, a fuel tank, etc. must be manufactured from materials with high air-tightness, and an opening and closing unit of the chamber also must have high air-tightness. Further, the inside of the chamber must be cleaned before and after measurement. For cleaning, the inside of the chamber is usually heated to about 60° C., and clean air is circulated within the chamber. Such cleaning process often takes several weeks.

In general, fuels, lubricants, pressure transmission fluids and the like are not single compositions, but mixtures. When testing fluid is a mixture, the chemical composition of the mixture tends to undergo change. For example, low-molecular compositions in the mixture often selectively permeate, resulting in lower content of the compositions in the mixture. Accordingly, in order to comprehend the whole state of a mixture permeating through a tubular specimen, an apparatus for permeability analysis is needed which is capable of determining permeability characteristics, while keeping the chemical composition of the mixture within a certain range.

Therefore, it is the first object of the present invention to provide an apparatus for permeability analysis suitable for determining permeability characteristics of a tubular specimen. The second object of the present invention is to provide an apparatus for permeability analysis having a measuring chamber whose materials are not required to have high air-tightness and/or whose opening and closing unit is not required to have higher air-tightness than conventional units.

The third object of the present invention is to provide an apparatus for permeability analysis at least part of which is disposable after every measurement. The fourth object of the present invention is to provide an apparatus for permeability analysis measuring the volume of the testing fluid permeating through the tubular specimen and determining permeability characteristics of the tubular specimen, while keeping the chemical composition of a testing fluid unchanged.

Other objects of the present invention will become clear from the explanation of the present invention below.

To achieve the objects described above, an apparatus for permeability analysis of one embodiment of the present invention is an apparatus for permeability analysis transmitting a testing fluid into a tubular specimen and measuring said testing fluid permeating through said tubular specimen, comprising a carrier gas supply unit, a cylindrical frame that is shorter than said tubular specimen and accommodates part in a certain length of said tubular specimen therein, two sealing joints that are located on each end of said cylindrical frame and are used to seal up the inner surface of said cylindrical frame and the outer surface of said tubular specimen, a carrier gas flow inlet leading from the outside of said cylindrical frame to the inside of said cylindrical frame, a carrier gas flow outlet leading from the inside of said cylindrical frame to the outside of said cylindrical frame, a detection device, and a pump, wherein one end of said tubular specimen and the other end of said tubular specimen are connected to each other via said pump and wherein said apparatus for permeability analysis circulates said testing fluid through said tubular specimen continuously or intermittently by means of said pump, introduces carrier gas supplied by said carrier gas supply unit to said carrier gas flow inlet, conveys said carrier gas flowing out of said carrier gas flow outlet to said detection device, and then measures the volume of said testing fluid contained in said carrier gas by means of said detection device.

The measuring chamber of the apparatus for permeability analysis of the present invention is a space formed between the tubular specimen and the cylindrical frame covering part in a certain length of the tubular specimen. The inner volume of the cylindrical frame is selectable depending on the outer shape (diameter, length, etc.) of the tubular specimen. The substantial inner volume of the measuring chamber is a limited space formed between the inner surface of the cylindrical frame and the outer surface of the tubular specimen. This allows the inner volume of the measuring chamber to be small, thereby keeping the dilution ratio of permeates which are the substances permeating through the tubular specimen at a low level.

The apparatus for permeability analysis of the present invention, which has the carrier gas flow inlet and the carrier gas flow outlet at the measuring chamber, conveys permeates from the measuring chamber to the detection device, together with the flow of carrier gas. This allows permeates to flow without staying in the measuring chamber, and even if they stay in the measuring chamber, the staying time is very short. Therefore, an opening and closing unit, i.e. the sealing joint, is not required to be high in air-tightness. This is in contrast to conventional apparatuses for permeability analysis that are required to have a measuring chamber with high air-tightness because permeates are left in the measuring chamber for a long time.

For the same reason, no high air-tightness is required of materials of the cylindrical frame, and there is no necessity for particular surface treatment on the inner surface of the cylindrical frame to prevent absorption of permeates. Therefore, metals and glasses that are not surface-treated are available as a cylindrical frame. Furthermore, a synthetic resin tube may be available as a cylindrical frame. These are advantages over the frames of conventional measuring chambers for which mainly surface-treated metals and glasses are used, and enable us to procure a measuring chamber, that is the cylindrical frame at low cost.

For at least the reasons described above, part of the apparatus for permeability analysis, i.e. the cylindrical frame, is disposable after every measurement, and the apparatus for permeability analysis need not always be cleaned before and after measurement when such part is disposed of. However, it should be appreciated that the measuring chamber may be used several times by cleaning the cylindrical frame, instead of replacing the cylindrical frame with a new one.

In the apparatus for permeability analysis of the present invention, the tubular specimen is longer than the cylindrical frame. A space formed between the inner surface of the cylindrical frame and the outer surface of the tubular specimen plays a major part in measurement, and both ends of the tubular specimen are outside the part involved in measurement. Both ends of said tubular specimen are connected to each other via a pump, and the testing fluid is circulated through the tubular specimen continuously or intermittently, during measuring period.

In general, in the case that a testing fluid is a mixture such as gasoline, diesel oil, and lubricant, low-molecular-weight compositions of such mixture tend to permeate selectively, thus often causing change in the chemical composition of said testing fluid during the measuring period. However, in the apparatus for permeability analysis of the present invention, where the testing fluid is circulated through the circulating system (including a tubular specimen, a pump, and a testing fluid pipe), it is possible to substantially neglect change in the chemical composition of the testing fluid during measuring period. A reservoir for the testing fluid may be placed in the circulating system. Thus, the apparatus for permeability analysis of the present invention is preferable specifically for testing fluid of mixture composition.

Because the ends of the tubular specimen are outside the measuring system, they do not always have to be completely connected and sealed.

In the apparatus for permeability analysis of the present invention, the tubular specimen is a hollow cylinder or a hollow pillar. The cross sections of the tubular specimen may be the same at its different positions in a longitudinal direction or may be different. The outside shape of the tubular specimen includes, for example, triangle pole, square pole, polygonal pole, circular cone, polygonal cone, and rod with elliptical cross section. The tubular specimen of the present invention may be flexible or may be inflexible. The tubular specimen of the present invention may be linear or may be curved. The tubular specimen of the present invention may be two or more tube members connected to each other.

More specific examples of the tubular specimen include, for example, pipe members for fuels, lubricants, and pressure transmission fluids used for automobiles, trucks, motorbikes, vessels, airplanes, etc. Vehicle fuels include, for example, gasoline, diesel oil, liquid natural gas, and ethanol-blended gasoline.

In the apparatus for permeability analysis of the present invention, the cylindrical frame is a hollow cylinder, a hollow polygonal cylinder, etc. that can accommodate a subject to be tested in the hollow space thereof.

In the apparatus for permeability analysis of the present invention, in the case that the testing fluid is a mixture, the permeability analysis includes: (1) measurement of the total volume of the testing fluid permeating through tubular specimen, (2) qualitative analysis of the testing fluid permeating through the tubular specimen, and (3) quantitative analysis of each composition of the testing fluid permeating through the tubular specimen.

In the apparatus for permeability analysis of the present invention, the testing fluids include, for example liquids such as gasoline, diesel oil, and lubricant and gases such as natural gas.

In the apparatus for permeability analysis of the present invention, the detection device includes, for example: (1) a gas chromatograph with a flame ionization detector (FID) as a detector, (2) a gas chromatograph with a mass spectrometer as a detector, (3) an FID, and (4) a mass spectrometer.

In the apparatus for permeability analysis of a preferred embodiment of the present invention, said carrier gas enters at said carrier gas flow inlet and flows out of said carrier gas flow outlet at all times during the measuring period.

In the apparatus for permeability analysis of this preferred embodiment, the permeates are transmitted, together with carrier gas, to the detection device; hence the substance is not left in the measuring chamber. Therefore, an opening and closing unit such as a sealing joint is not required to be high in air-tightness. For the same reason, materials of the cylindrical frame are not required to be high in air-tightness. These features enable us to procure a measuring chamber that has a cylindrical frame at low price. Furthermore, these features make it very easy for the cylindrical frame to be disposed of after every measurement.

In the apparatus for permeability analysis of a preferred embodiment of the present invention, said cylindrical frame is divided into parts in the direction parallel to the central axis extending in a longitudinal direction thereof.

In the case that the tubular specimen has the different cross-sectional shape or cross-sectional area at the different positions in a longitudinal direction thereof (for example, a fitting of a tube, a curved tube, etc.), the apparatus for permeability analysis makes it possible to make the substantial inner volume of the measuring chamber smaller by forming a cylindrical frame according to the outer shape of such subject to be tested. Further, the tubular specimen may be easily accommodated in the measuring chamber.

The wording of "divided into parts in the direction parallel to the central axis extending in a longitudinal direction" means "can be divided into two or more longitudinal parts." Preferably the cylindrical frame is divided into two parts on the plane including the central axis. However, it may not be divided into two symmetric shapes, i.e., it may be divided into a part containing the central axis and a part not containing the central axis. Preferably the divided plane is flat. However, it may be curved or bent.

The curved cylindrical frame often may have two or more linear central axes. For example, a dogleg cylindrical frame is acceptable.

In the apparatus for permeability analysis of a preferred embodiment of the present invention, said cylindrical frame is a flexible cylindrical frame made from synthetic resin materials.

Because the cylindrical frame of the preferred embodiment of the present invention is flexible, even a curved tubular specimen can be easily threaded into such a flexible cylindrical frame. Such synthetic resins that offer a flexible cylindrical frame include, for example, polytetrafluoroethylene, polyvinyl chloride, polyethylene, and polypropylene.

The present invention, the preferred embodiments of the present invention, and the components included therein as described above may be embodied in other specific forms when they are combined to as much an extent as possible.

The apparatus for permeability analysis of the present invention is the apparatus for permeability analysis preferable for measuring permeability characteristics of a tubular specimen, wherein materials for the measuring chamber are not required to be high in air-tightness, and/or the opening and closing unit of the measuring chamber is not required to be higher in air-tightness than measuring chambers of conventional similar apparatus.

In the apparatus for permeability analysis of the present invention, at least part of the apparatus is disposable after every measurement, thus relieving the user of time-consuming and troublesome cleaning work. Furthermore, the apparatus for permeability analysis of the present invention is preferable specifically for testing fluid of a mixture composition.

DESCRIPTION OF THE PREFERRED EMBODIMENT

With reference to the following figures, a description will be made of the apparatus for permeability analysis of the present invention. Measurements, materials, shapes, relative positions, etc. of the members and parts described in the embodiments of the present invention are merely examples and are not intended to restrict the scope of the present invention thereto, except as specifically described.

Figure 1:
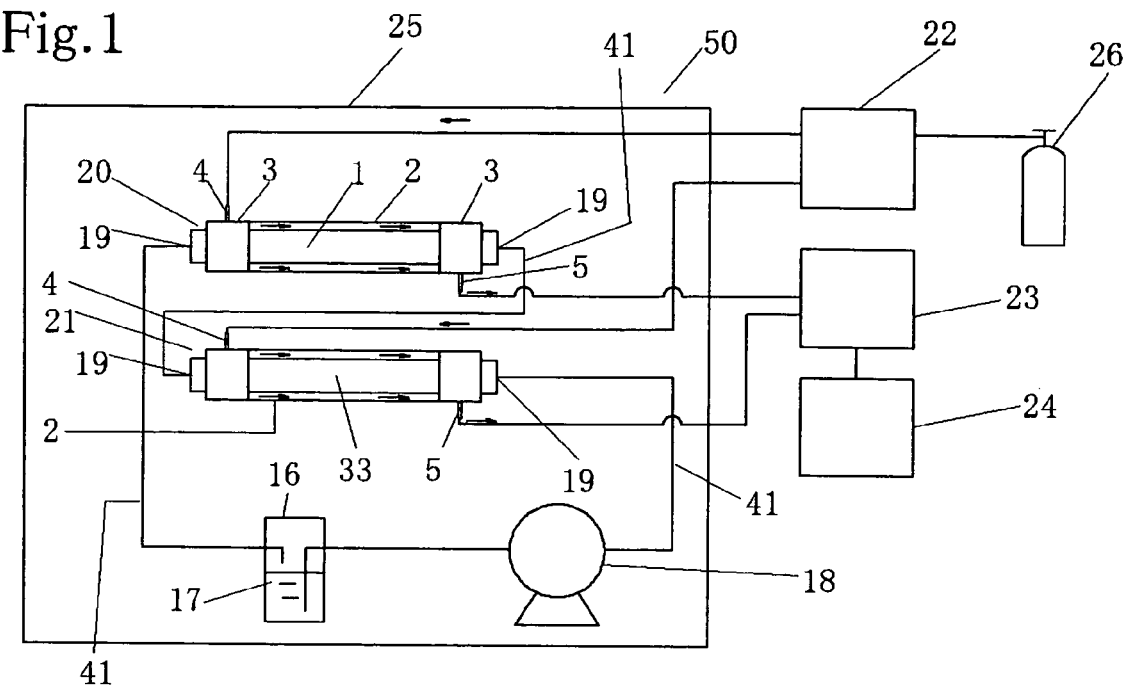
FIG. 1 is a schematic diagram of the apparatus for permeability analysis of the present invention.
Figure 2:
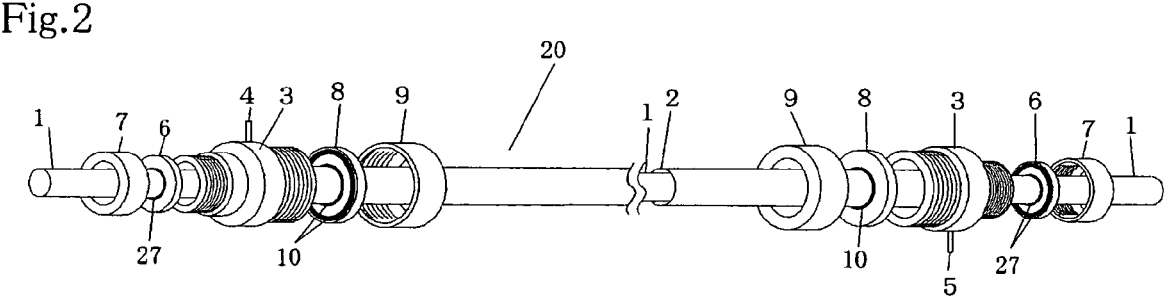
FIG. 2 is an exploded perspective view of the first measuring chamber 20 of the apparatus for permeability analysis of the present invention.

FIG. 1 is a schematic diagram of the apparatus for permeability analysis 50. FIG. 2 is an exploded perspective view of the first measuring chamber 20, which is one of the components constituting the apparatus for permeability analysis 50. The apparatus for permeability analysis 50 is an apparatus for permeability analysis for tubular specimens used for vehicle fuel, which performs a bipartite determination of permeability characteristics of the first tubular specimen 1 and the second tubular specimen 33.

Part in a certain length of the first tubular specimen 1 is accommodated in the internal part of a cylindrical frame 2. A first measuring chamber 20 is the space between the inner surface of the cylindrical frame 2 and the outer surface of the first tubular specimen 1. Part in a certain length of the second tubular specimen 33 is accommodated in a cylindrical frame 2. A second measuring chamber 21 is the space between the inner surface of the cylindrical frame 2 and the outer surface of the second tubular specimen 33. The first measuring chamber 20 and the second measuring chamber 21 are the same.

With reference to FIG. 2, a description will be made of the first measuring chamber 20. Part in the certain length of the first tubular specimen 1, is accommodated in the internal part of the cylindrical frame 2. The cylindrical frame 2 is a polytetrafluoroethylene resin tube. The material of the cylindrical frame 2 may be also synthetic resin (for example, polyvinyl chloride, polyethylene, and polypropylene), metal (for example, aluminum and stainless steel such as SUS314), glass or the like. The cylindrical frame 2 made of synthetic resin, metal, glass or the like may be treated on its inner surface for absorption protection or may not be treated. Polytetrafluoroethylene resin is most preferable among these materials, because it is flexible and its surface is inactive.

Any cross-sectional inner diameter of the cylindrical frame 2 is acceptable if the diameter is longer than the cross-sectional outside diameter of the first tubular specimen 1. Preferably said cross-sectional inner diameter is equal to or less than 10 mm longer than said cross-sectional outside diameter, more preferably said cross-sectional inner diameter is equal to or less than 5 mm longer than said cross-sectional outside diameter.

A connecting joint 3 that has a different diameter at each side thereof is arranged at each end of the cylindrical frame 2, and a large nut 9 is screwed up, via a large sleeve 8, on one end of the connecting joint 3. Each end of the cylindrical frame 2 is sealed and fixed on the connecting joint 3. Each of the large sleeves 8 acts to support the sealing, and in this embodiment, a large O-ring 10 made from synthetic rubber is attached to the large sleeve 8.

At the other end of the connecting joint 3 is a small nut 7 screwed up via a small sleeve 6. The outer surface of the first tubular specimen 1 is sealed and fixed on the connecting joint 3. The small sleeve 6 acts to support the sealing, and in this embodiment, a small O-ring 27 made from synthetic rubber is attached to the small sleeve 6. This arrangement allows the inner surface of the cylindrical frame 2 and the outer surface of the first tubular specimen 1 to be sealed up.

A carrier gas flow inlet 4 is mounted on one of the connecting joints 3, and a carrier gas flow outlet 5 is mounted on the other of the connecting joints 3. The carrier gas flow inlet 4 and the carrier gas flow outlet 5 each lead to the space formed between the inner surface of the cylindrical frame 2 and the outer surface of the first tubular specimen 1. Carrier gas introduced from the carrier gas flow inlet 4 flows through the space formed between the inner surface of the cylindrical frame 2 and the outer surface of the first tubular specimen 1 and carries the testing fluid permeating through the first tubular specimen 1 from the carrier gas flow outlet to the outside of the first measuring chamber 20.

Unification of the carrier gas flow inlet 4 and the connecting joint 3 and unification of the carrier gas flow outlet 5 and the connecting joint 3 offer an advantage that it is possible to replace only the cylindrical frame 2. However, in the measuring chamber of the present invention, the carrier gas flow inlet 4 and the carrier gas flow outlet 5 may be mounted directly on the cylindrical frame.

A mixture such as gasoline, artificially arranged gasoline, and lubricant may be used as testing fluid.

In FIG. 1, the first tubular specimen 1 and the second tubular specimen 33 are connected in series through connection ports 19 and a testing fluid pipe 41. The closed flow path system for testing fluid is comprised of the inner space of the first tubular specimen 1, the inner space of the second tubular specimen 33, a reservoir 16, a pump 18, and a testing fluid pipe 41. During a measuring period, testing fluid 17 (artificially arranged gasoline in this embodiment), in the reservoir 16 is continuously circulated through the inner space of the first tubular specimen 1 and the inner space of the second tubular specimen 33 by the pump 18.

Because both connecting ports 19 that are positioned at each end of the first tubular specimen 1 are located outside the first measuring chamber 20, the connecting port 19 may be low in air-tightness.

Carrier gas that is helium gas in this embodiment, is transmitted to the carrier gas flow inlet 4 of the first measuring chamber 20 through a flow controller 22 from a carrier gas cylinder 26. The carrier gas flows through a space formed between the inner surface of the cylindrical frame 2 and the outer surface of the first tubular specimen 1 and runs through the carrier gas flow outlet 5, and then reaches a sampling unit 23. In this manner, substances permeating through the first tubular specimen 1 reach the sampling unit 23, while being guided by the flow of the carrier gas.

At the same time, carrier gas that is helium gas in this embodiment, is transmitted to the carrier gas flow inlet 4 of the second measuring chamber 21 through the flow controller 22 from the carrier gas cylinder 26. The carrier gas flows through a space formed between the inner surface of the cylindrical frame 2 and the outer surface of the second tubular specimen 33 and runs through the carrier gas flow outlet 5, and then reaches the sampling unit 23. In this manner, substances permeating through the second tubular specimen 33 reach the sampling unit 23, while being guided by the flow of the carrier gas.

Carrier gas is supplied to the first measuring chamber 20 and the second measuring chamber 21 at all times during measuring period. Consequently, the permeates are not left in the first measuring chamber 20 and the second measuring chamber 21, which situation does not require that the chambers be tightly sealed up. The permeates are transmitted to a detection device 24, which is a gas chromatograph with a FID in this embodiment, through the sampling unit 23 to be separated and determined.

Figure 3:
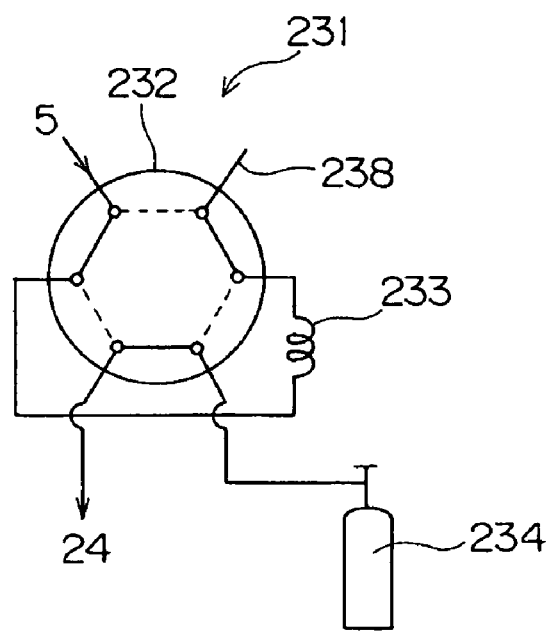
FIG. 3 is a view showing a sampling unit of one measuring channel.

FIG. 3 is a view showing a sampling unit of one channel 231 used for the first measuring chamber 20. A sampling unit of one channel 231 has a switching valve 232. The switching valve 232 switches from the connection shown in solid lines to the connection shown in dashed lines and vice versa. A pipe extended from the carrier gas flow outlet 5, a measuring pipe 233, an exhaust outlet 238, a pipe extended from a gas cylinder for a gas chromatograph, and a pipe directed to the gas chromatograph 24 are connected to the switching valve 232.

During the waiting period before detection, the switching valve 232 is held at the connecting position shown in solid lines. In this state, permeates (substances permeating through the first tubular specimen 1) and carrier gas introduced from the carrier gas flow outlet 5 run through the measuring pipe 233 and then are exhausted from the exhaust outlet 238.

At the beginning of detection, the switching valve 232 is switched to the connecting position shown in dashed lines. Permeate and carrier gas present in the measuring pipe 233 at the time of switching are transmitted to the gas chromatograph 24, while being guided by the flow of the gas supplied from a gas cylinder 234.

After that, the switching valve 232 is switched over to the connecting position shown in solid lines.

For one measuring chamber, one detection process is performed using the detection device 24, for example, every two hours. One detection process takes, for example, 15 minutes. The apparatus for permeability analysis 50 has two sampling units of one measuring channel 231 described above. The sampling unit 23, which contains two of the sampling units of one measuring channel 231, transmits either of the carrier gas containing permeate from the first measuring chamber 20 or the carrier gas containing permeate from the second measuring chamber 21, to the detection device 24, i.e. gas chromatograph, delaying the timing of transmitting. Then the detection device 24 detects the concentration of the permeates.

The detection device 24 is not limited to a gas chromatograph with FID. For example, a gas chromatograph with mass spectrometer is also acceptable. When separation and quantitative analysis are not required, a FID or a mass spectrometer is solely usable without a chromatography unit.

A data processor, which is not shown in the figure, computes permeability, etc. of the first tubular specimen 1 and the second tubular specimen 33 on the basis of the concentration of the permeates obtained.

In general, the permeability varies with the temperature of a tubular specimen and a testing fluid. Therefore, the first measuring chamber 20, the second measuring chamber 21, the reservoir 16, and the pump 18 are usually located in the constant-temperature bath 25.

In the first measuring chamber 20 of the embodiment, a first tubular specimen 1 made from nylon of 4 mm in inner diameter, 6 mm in outer diameter, and 1000 mm in length and a cylindrical frame 2 made from polytetrafluoroethylene of 8 mm in inner diameter, 10 mm in outer diameter, and 900 mm in length were used. Carrier gas flow rate was set at 30 ml/min. The same was applied to the second measuring chamber 21.

In general, the volume of a testing fluid permeating through a tubular specimen gradually increases with the passage of time at the early stage of measurement and then becomes stable. In general, the permeability determination is repeatedly carried out until the concentrations obtained by the measurements at regular intervals become stable. For example, in the case that a tubular specimen is made from nylon, polyethylene or other synthetic resins and the testing fluid is artificially arranged gasoline, it takes approximately one day for the detected value of the permeate to become stable. Furthermore, in the case that the tube is a high barrier tube and the testing fluid is artificially arranged gasoline, it takes approximately one week to several months for the detected value of the permeate to become stable.

It is appreciated that the "measuring period" regarding the circulation of the testing fluid and the carrier gas flow through the measuring chamber, means the period from the beginning of the first waiting period to the ending of the last detection process, for the one tubular specimen. The "measuring period" may continue minutes, hours, days, weeks or months depending upon materials of tubular specimen, testing fluid, purpose of the particular permeability analysis, etc.

The above explanation is made of a bipartite apparatus for permeability analysis for measuring the permeability characteristics of two tubular specimens simultaneously; however, the apparatus for permeability analysis of the present invention is not limited to bipartite analysis, i.e., apparatus for permeability analysis with appropriate quantity (such as one, three, and six) of measuring chambers are to be considered within the scope of the present invention.

Figure 4:
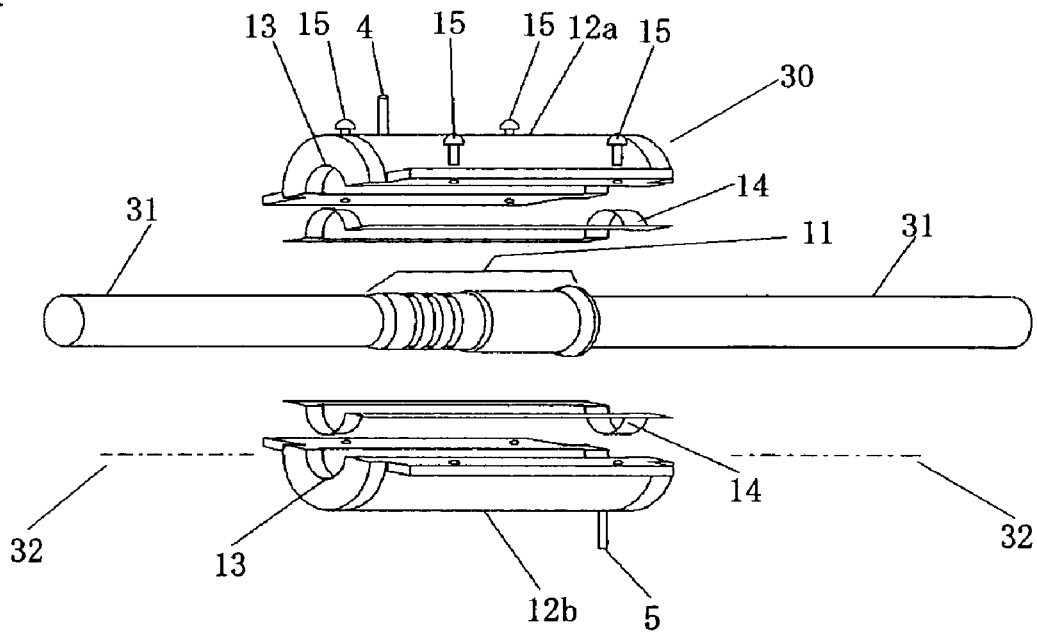
FIG. 4 is an exploded perspective view of a third measuring chamber 30 of another embodiment of the present invention.

FIG. 4 is an exploded perspective view of a third measuring chamber 30 of another embodiment of the present invention. A certain length part of the third tubular specimen 31 is accommodated in the internal part of the cylindrical frame that comprises a divided, cylindrical frame 12a and a divided, cylindrical frame 12b. The third tubular specimen 31 is a fuel tube. The third tubular specimen 31 has a tube joint 11. The third tubular specimen 31 consists of two tubes coupled to each other, where one tube is inserted in the inner space of the other tube via an O-ring and a slip prevention mechanism, and the other tube is heat shrunken.

The divided, cylindrical frame 12a and the divided, cylindrical frame 12b may be made from synthetic resin, metal (for example, aluminum and stainless steel such as SUS314) or the like.

The cylindrical frame of the third measuring chamber 30, which is divided into two parts in the direction parallel to the central axis (shown by a line segment 32 in the figure) extending in a longitudinal direction thereof, comprises a divided, cylindrical frame 12a and a divided, cylindrical frame 12b. A packing 14 serves to seal up the gap between the divided, cylindrical frame 12a and the divided, cylindrical frame 12b. A tube contacting part 13 seals up a gap between the cylindrical frame and the outer surface of the third tubular specimen 31. The gap between the inner surface of the cylindrical frame and the outer surface of the third tubular specimen 31 is sealed up by sandwiching of the third tubular specimen 31 between the divided, cylindrical frame 12a and the divided, cylindrical frame 12b and screwing screws 15.

The carrier gas flow inlet 4 is mounted on the divided, cylindrical frame 12a, and the carrier gas flow outlet 5 is mounted on the divided, cylindrical frame 12b. The carrier gas flow inlet 4 and the carrier gas flow outlet 5 communicate with each other via the space that is formed between the inner surface of the cylindrical frame and the outer surface of the third tubular specimen 31.

The cylindrical frame, which is divided into the divided, cylindrical frame 12a and the divided, cylindrical frame 12b, is preferable, in particular when a cylindrical tubular specimen has different diameters at different parts thereof or when it is bended. In this case, the third measuring chamber 30 is used instead of the first measuring chamber 20 of the apparatus for permeability analysis 50 described in FIG. 1.

Figure 5:
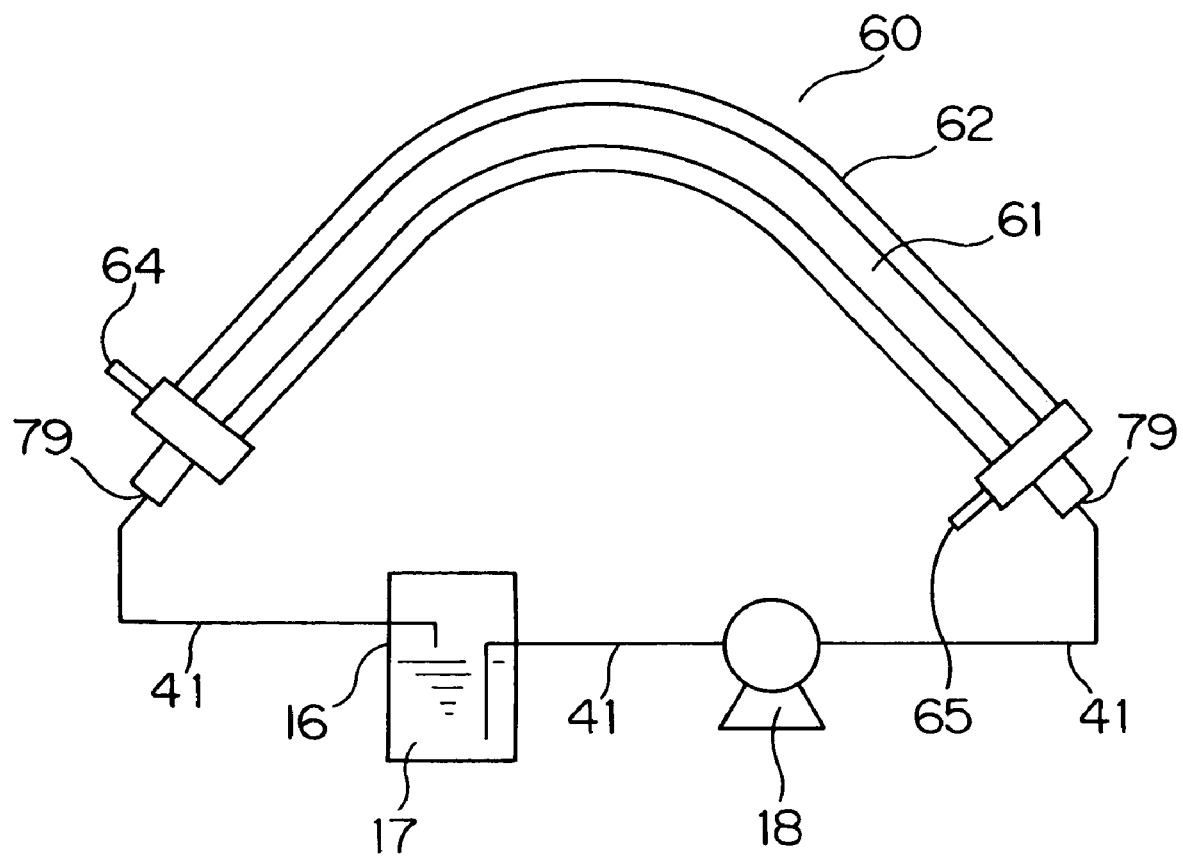
FIG. 5 is a schematic diagram of a fourth measuring chamber 60 of another embodiment of the present invention.

FIG. 5 is a schematic diagram of a fourth measuring chamber 60 of another embodiment of the present invention. A curved fourth tubular specimen 61 is accommodated in a cylindrical frame 62 made from a flexible material of synthetic resin (polytetrafluoroethylene).

The cylindrical frame 62, which is made from the flexible material as described above, enables the determination of permeability characteristics of a curbed tubular specimen as is. Therefore, it is expected that the permeability characteristics of a curved part of a tubular specimen having a strain caused in the manufacturing process can be determined at a level close to the situation where the tubular specimen is actually used.

Near each end of the cylindrical frame 62, the carrier gas flow inlet 64 and the carrier gas flow outlet 65 are arranged. Connecting ports 79, which are at each end of the tubular specimen 61, communicate with each other via a pump 18, a reservoir 16, and a testing fluid pipe 41. The fourth measuring chamber 60 is used instead of the first measuring chamber 20 of the apparatus for permeability analysis 50 described in FIG. 1.

What is claimed is:

1. An apparatus for permeability analysis transmitting a testing fluid into a tubular specimen and measuring said testing fluid permeating through said tubular specimen, comprising;

a carrier gas supply unit, a cylindrical frame that is shorter than said tubular specimen and accommodates part in a certain length of said tubular specimen therein, two sealing joints that are located on each end of said cylindrical frame and are used to seal up the inner surface of said cylindrical frame and the outer surface of said tubular specimen, a carrier gas flow inlet leading from the outside of said cylindrical frame to the inside of said cylindrical frame, a carrier gas flow outlet leading from the inside of said cylindrical frame to the outside of said cylindrical frame, a detection device, and a pump, wherein one end of said tubular specimen and another end of said tubular specimen are connected to each other via said pump, and wherein said apparatus for permeability analysis circulates said testing fluid through said tubular specimen continuously or intermittently by means of said pump, introduces carrier gas supplied by said carrier gas supply unit to said carrier gas flow inlet, conveys said carrier gas flowing out of said carrier gas flow outlet to said detection device, and then measures the volume of said testing fluid contained in said carrier gas by means of said detection device.

2. An apparatus for permeability analysis according to claim 1, wherein said carrier gas enters at said carrier gas flow inlet and flows out of said carrier gas flow outlet at all times during a measuring period.

3. An apparatus for permeability analysis according to claim 1, wherein said cylindrical frame is divided into parts in the direction parallel to the central axis extending in a longitudinal direction thereof.

4. An apparatus for permeability analysis according to claim 1, wherein said cylindrical frame is a flexible cylindrical frame made from synthetic resin materials.

* * * * *